(12) United States Patent
Okada et al.

(10) Patent No.: US 8,216,608 B2
(45) Date of Patent: Jul. 10, 2012

(54) GASTRIC ANTACID

(75) Inventors: Akira Okada, Kagawa (JP); Keiko Katsuki, Kagawa (JP)

(73) Assignee: Kyowa Chemical Industry Co., Ltd., Takamatsu-Shi (JP)

( * ) Notice: Subject to any disclaimer, the term of this patent is extended or adjusted under 35 U.S.C. 154(b) by 746 days.

(21) Appl. No.: 12/086,691

(22) PCT Filed: Dec. 14, 2007

(86) PCT No.: PCT/JP2007/074112
§ 371 (c)(1),
(2), (4) Date: Aug. 19, 2008

(87) PCT Pub. No.: WO2008/075621
PCT Pub. Date: Jun. 26, 2008

(65) Prior Publication Data
US 2009/0142394 A1    Jun. 4, 2009

(30) Foreign Application Priority Data
Dec. 20, 2006  (JP) .................................. 2006-341990

(51) Int. Cl.
*A61K 9/20* (2006.01)
*A61K 33/30* (2006.01)
*A61K 33/00* (2006.01)

(52) U.S. Cl. ............... 424/464; 423/593.1; 423/594.14; 514/819; 514/925; 514/926

(58) Field of Classification Search .................. None
See application file for complete search history.

(56) References Cited

U.S. PATENT DOCUMENTS

| | | | |
|---|---|---|---|
| 3,539,306 A | 11/1970 | Kumura et al. | |
| 3,650,704 A | 3/1972 | Kumura et al. | |
| 4,970,064 A * | 11/1990 | Adam et al. | 424/49 |
| 6,117,868 A * | 9/2000 | Pfirrmann | 514/222.5 |
| 6,287,532 B1 | 9/2001 | Okada et al. | |
| 6,297,193 B1 | 10/2001 | Miyata et al. | |
| 6,313,208 B1 | 11/2001 | Nosu et al. | |

FOREIGN PATENT DOCUMENTS

| | | |
|---|---|---|
| EP | 0 040 364 A1 | 11/1981 |
| JP | 8-291011 A | 11/1996 |
| JP | 10-182315 A | 7/1998 |
| JP | 11-180808 A | 7/1999 |
| JP | 11-222494 A | 8/1999 |
| JP | 11-240886 A | 9/1999 |
| JP | 2000-159520 A | 6/2000 |
| JP | 2004-225052 A | 8/2004 |
| JP | 2006-131581 A | 5/2006 |
| JP | 2008-120703 A | 5/2008 |

OTHER PUBLICATIONS

S. H. Wong et al.; Protection by Zinc Sulphate against Ethanol-Induced Ulceration: Preservation of the Gastric Mucoscal Barrier; Pharmacology, 1986, vol. 33, No. 2, 1986, pp. 94-102.
Supplementary European Search Report issued on May 5, 2010 in corresponding European patent application No. 07850616.

* cited by examiner

*Primary Examiner* — Lakshmi Channavajjala
(74) *Attorney, Agent, or Firm* — Birch, Stewart, Kolasch & Birch, LLP

(57) ABSTRACT

A novel particulate composite hydrotalcite which offers antacidic effect comparable to that of a particulate hydrotalcite so far used as a gastric antacid and, further, offers excellent stomach inner wall protection effect. A particulate composite hydrotalcite represented by the following formula (1), $$(Mg_aZn_b)_{1-x}Al_x(OH)_2(A^{n-})_{x/n} \cdot mH_2O \qquad (1)$$

wherein $A^{n-}$ is $CO_3^{2-}$, $SO_4^{2-}$ or $Cl^-$, n is 1 or 2, and x, a, b and m are values that satisfy the following conditions, $0.18 \leq x \leq 0.4$, $0.5 \leq a < 1$, $0 < b \leq 0.5$, $0 \leq m < 1$, and a gastric antacid using the particulate composite hydrotalcite as an effective component. When used as a gastric antacid, the particulate composite hydrotalcite suppresses the occurrence of damage in the mucous membranes of stomach and intestines.

6 Claims, No Drawings

GASTRIC ANTACID

TECHNICAL FIELD

This invention relates to a gastric antacid containing a particulate composite hydrotalcite as an effective component. More particularly, the invention relates to a novel gastric antacid using a particulate zinc-containing composite hydrotalcite as an effective component exhibiting an antacidic effect similar to that of the conventional particulate hydrotalcite and having an excellent effect for protecting the inner wall of the stomach.

BACKGROUND ART

A particulate hydrotalcite has heretofore been produced and sold as a medicinal antacid in the form of tablets, granules and capsules. Ideal requirements for the gastric antacid are that the effect is immediately exhibited to elevate the pH of gastric juice up to about 3 within a minute after the internal use thereof, the pH is maintained between 3 and 5 for extended periods of time, the gastric juice is not caused to become alkaline even if the gastric antacid is internally used in excess amounts, and that the antacid does not cause constipation, diarrhea or alkalosis, does not permit antacidic property to be impaired by pepsin, and does not permit the antacidic property to be changed by water and temperature. In order to satisfy the above requirements, a particulate hydrotalcite was, developed as a gastric antacid.

The particulate hydrotalcite as a gastric antacid and a method of preparation thereof have been disclosed in U.S. Pat. No. 3,650,704 and U.S. Pat. No. 3,539,306. The particulate hydrotalcite effective as a gastric antacid is typically represented by $Mg_6Al_2(OH)_{16}CO_3 \cdot 4H_2O$.

When internally used for extended periods of time, however, the conventional particulate hydrotalcite often used to damage the mucous membrane of the internal wall of stomach.

DISCLOSURE OF THE INVENTION

Problems to be Solved by the Invention

The particulate hydrotalcite serves as an excellent gastric antacid but may often damage the mucous membrane of the internal wall of stomach if it is used for extended periods of time, and leaves much room for improvement from the standpoint of protecting the internal wall of stomach. It is therefore an object of the present invention to provide improved particulate hydrotalcite effective for use as a gastric antacid exhibiting excellent activity for protecting the inner wall of stomach, i.e., having effect for preventing ulcer.

Means for Solving the Problem

The present inventors have forwarded the study to improve the particulate hydrotalcite in an attempt to achieve the above object.

As a result, the inventors have discovered that a particulate composite hydrotalcite comprising the particulate hydrotalcite which contains Zn in a very small and particular amount as a solid solution exhibits excellent antacidic action protecting the mucous membrane of stomach and preventing ulcer from occurring in the internal wall of stomach.

That is, the present inventors have discovered that the particulate composite hydrotalcite of the following formula (1) obtained by solidly dissolving a very small amount of zinc ions which are relatively inexpensive and non-toxic or relatively lowly toxic in the particulate hydrotalcite, is effective as a gastric antacid protecting the inner wall of stomach and exhibiting excellent antacidic effect, i.e., is effective for protecting the mucous membrane of stomach and for preventing stomach ulcer, and have thus arrived at the present invention,

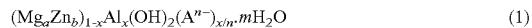

$$(Mg_aZn_b)_{1-x}Al_x(OH)_2(A^{n-})_{x/n} \cdot mH_2O \quad (1)$$

wherein $A^{n-}$ is $CO_3^{2-}$, $SO_4^{2-}$ or $Cl^-$, n is 1 or 2, and x, a, b and m are values that satisfy the following conditions, $0.18 \leq x \leq 0.4$, $0.5 \leq a < 1$, $0 < b \leq 0.5$, $0 \leq m < 1$.

The particulate composite hydrotalcite of the present invention represented by the formula (1) is a novel compound discovered by the present inventors and comprises a particulate hydrotalcite containing a very small amount of zinc (Zn) solidly dissolved therein. Therefore, the particulate composite hydrotalcite is a compound having the same crystalline structure as that of the known particulate hydrotalcite, and exhibits nearly the same diffraction pattern as that of the particulate hydrotalcite as measured by the powder X-ray diffraction method. Further, the particulate composite hydrotalcite of the present invention contains zinc that is solidly dissolved in the hydrotalcite and does not damage the internal wall of stomach or the internal wall of intestines.

The particulate composite hydrotalcite of the present invention has a chemical structure represented by the above formula (1). The formula (1) will now be concretely described. In the formula (1), $A^{n-}$ is an anion having a valency of n, and is $CO_3^{2-}$, $SO_4^{2-}$ or $Cl^-$, and is, preferably, $CO_3^{2-}$ or $SO_4^{2-}$, and is, most preferably, $CO_3^{2-}$. These anions may include two kinds, e.g., $CO_3^{2-}$ and $SO_4^{2-}$, simultaneously. Here, x should satisfy $0.18 \leq x \leq 0.4$ and is, preferably, $0.2 \leq x \leq 0.35$ and, more preferably, $0.24 \leq x \leq 0.3$. Further, b should satisfy $0 < b \leq 0.5$ and is, preferably, $0.0005 \leq b \leq 0.2$ and, particularly preferably, $0.0006 \leq b \leq 0.1$. Further, a should satisfy $0.5 \leq a < 1$, and, more preferably, $0.6 \leq a \leq 0.9$. Further, m stands for the content of crystal water and satisfies $0 \leq m < 1$ and, preferably, $0.1 \leq m \leq 1$.

The method of producing the particulate composite hydrotalcite of the present invention is basically the same as the known method of producing the particulate hydrotalcite (e.g., U.S. Pat. No. 3,539,306). Here, zinc (Zn) is added to the starting material together with a magnesium salt and/or an aluminum salt so as to be contained therein as a solid solution. Zinc (Zn) should be added in a predetermined amount to the starting material, preferably, in the form of a water-soluble salt such as nitrate, sulfate or chloride, and the reaction conditions are selected from those in a range described in the above U.S. patent.

The method of producing the particulate composite hydrotalcite of the present invention comprises bringing an aqueous solution containing, for example, salts of Mg, Zn and Al (nitrate, chloride and sulfate) at ratios of metal elements that constitute the desired hydrotalcite, an aqueous solution of sodium carbonate ($Na_2CO_3/Al = 0.35$ to $0.75$) and an aqueous solution of sodium hydroxide into contact with each other, so as to be co-precipitated while holding the pH of the reaction solution at 10 to 10.5 with the aqueous solution of sodium hydroxide. The reaction is conducted at room temperature to 100° C. The reaction product can be used in its form or may be washed, and the suspension thereof (aqueous system) may be subjected to the hydrothermal reaction at a temperature of 70 to 200° C. for 0.5 to 24 hours.

The content of Na can be decreased by washing the reaction product with an increased amount of water or by washing the reaction product with an aqueous solution containing acids (hydrochloric acid, nitric acid, acetic acid and so on) in amounts of $10^{-3}$ to $10^{-5}$ mol/L (de-ionized water) in an amount 20 to 50 times as large as the weight of the particulate composite hydrotalcite.

Though there is no particular limitation on the shape of the particulate composite hydrotalcite of the present invention, it is advantageous if the particles have an average secondary particle size of 0.3 to 20 μm and, preferably, 0.4 to 10 μm as measured by the laser diffraction scattering method, and it is desired that particles has a BET specific surface area of 10 to 100 m²/g and, preferably, 10 to 50 m²/g.

When used as a gastric antacid, the particulate composite hydrotalcite of the invention can be used in any form such as powder, granule, tablet, capsule or slurry, and, as required, there can be added a vehicle, a bonding agent, a breaking agent and a lubricant thereto.

When orally administered as the gastric antacid, the particulate composite hydrotalcite of the present invention is administered in amounts and in a manner which are basically the same as those of the conventional particulate hydrotalcite. The amount of administration is in a range of 0.2 to 5 g and, preferably, 1 to 4 g per an adult a day.

The particulate composite hydrotalcite of the invention works as an excellent gastric antacid like the conventional particulate hydrotalcite. That is, the effect is immediately exhibited, the pH of gastric juice is maintained between 3 and 5 for extended periods of time, the gastric juice is not caused to become alkaline even if it is internally used in excess amounts, no constipation, diarrhea or alkalosis is caused, and antacidic property is not impaired by pepsin. In addition to the above advantages of the gastric antacid, the particulate composite hydrotalcite of the invention when internally used suppresses or prevents damage to the mucous membrane of the internal wall of stomach. As will become obvious from experiment described later, this effect is very excellent and astonishing over the effect obtained by the conventional particulate hydrotalcite. It is presumed that the above distinguished effect is exhibited by zinc (Zn) which is contained in very small amounts as a solid solution as represented by the above formula (1).

When internally used as a gastric antacid, therefore, the particulate composite hydrotalcite of the present invention helps attain the effect as the gastric antacid as well as the effect for protecting the mucous membranes of the internal wall of stomach and the internal walls of intestines simultaneously, also contributing to preventing the occurrence of ulcer in the internal wall of stomach and in the internal wall of intestines.

The invention will now be described in detail by way of Examples.

In Examples, (a) Zn, Na of the particulate composite hydrotalcite, (b) gastric antacid capacity test, and (c) Rossett-Rice test, stands for values measured by the methods described below.

(a) Analysis of Zn and Na.

Measured by the atomic absorptiometric method.

(b) Gastric Antacid Capacity Test.

200 mg of the sample was added to 100 ml of 0.1-N HCl, and was shaken at 37° C. for one hour. Thereafter, 50 ml thereof was back-titrated with 0.1-N NaOH to find the antacid capacity.

(c) Rossett-Rice Test.

70 ml of 0.1-N HCl and 30 ml of water were introduced into a beaker of a volume of 400 ml, and were stirred at about 200 rpm while being immersed in a constant-temperature bath maintained at 37° C. In this state, into the beaker were simultaneously added 1.0 g of the sample and 0.1-N HCl at a rate of 4.0 ml a minute, and the pH was continuously recorded until the pH of the system became lower than 3.0 to find the time until the pH reached 3, to find a maximum pH, to find the Rossett-Rice time, i.e., the time in which the pH was adjusted to be 3 to 5, and to find the acid rebound time, i.e., the time in which the pH became not smaller than 5.

(d) Average Secondary Particle Size.

Measured by using the MICROTRACK particle size profile meter, SPA-type (manufactured by Leeds & Northrupp Instruments Co.).

700 mg of a sample powder was added to 70 ml of water, was treated with ultrasonic waves (Model US-300 manufactured by Nissei Co., current of 300 μA) for 3 minutes and, thereafter, 2 to 4 ml of the dispersion solution was picked up and was added into a sample chamber of the particle size profile meter containing 250 ml of deaerated water. Thereafter, the analyzer was operated to circulate the suspension for 8 minutes to measure the particle size profile. Measurement was taken a total of two times, and an arithmetic mean value of 50% cumulative secondary particle sizes obtained through the measurement was calculated to regard it as an average secondary particle size of the sample.

(e) BET Specific Surface Area.

Measured by the adsorption method using liquid nitrogen.

(f) Powder X-Ray Diffraction Measuring Method.

$CuK_\alpha$ angle (2θ): 5 to 65°, step; 0.02, scan speed; 4°/min, tube voltage; 40 KV, tube current; 20 mA, apparatus; RINT 2200V X-ray diffraction system (manufactured by Rigaku Denki Co.).

EXAMPLE 1

A mixed aqueous solution {referred to as solution A} of magnesium nitrate of a concentration of 1.50 mol/L, zinc nitrate of a concentration of $3.61 \times 10^{-3}$ mol/L and aluminum nitrate of a concentration of 0.752 mol/L, an aqueous solution {solution B} of sodium carbonate of a concentration of 0.40 mol/L, and an aqueous solution {solution C} of sodium hydroxide of a concentration of 3.4 N were prepared. Next, by using a metering pump, the solution A and the solution B were poured into a reaction vessel at such flow rates that the volume ratio of the solution A and the solution B was 1 and 1, and the pH value of the reaction solution was adjusted with the solution C so as to be maintained in a range of 10 to 10.5, and the reaction was carried out at a temperature of 40° C. to form a precipitate. The precipitate was filtered, washed, dried overnight at 110° C., pulverized and was sieved to obtain a particulate composite hydrotalcite of the following composition. The washing consisted of washing with water and, then with hydrochloric acid of $10^{-3}$ mol/L. The amount of hydrochloric acid at this moment was 30 times as great as the weight of the particulate composite hydrotalcite.

Composition: $Mg_{0.665}Zn_{0.0016}Al_{0.333}(OH)_2(CO_3)_{0.167}\cdot 0.5H_2O$

The analytical results of Zn and Na in the particulate composite hydrotalcite and the tested results of the antacid capacity were as shown in Table 1, and the results of the Rossett-Rice test were as shown in Table 2.

EXAMPLE 2

A mixed aqueous solution {solution A} of magnesium nitrate of a concentration of 1.50 mol/L, zinc nitrate of a concentration of $2.01 \times 10^{-2}$ mol/L and aluminum nitrate of a concentration of 0.76 mol/L, an aqueous solution {solution B} of sodium carbonate of a concentration of 0.46 mol/L, and an aqueous solution {solution C} of sodium hydroxide of a concentration of 3.4 N were prepared. Next, the reaction was carried out in the same manner as in Example 1 to obtain a particulate composite hydrotalcite of the following composition. The washing consisted of washing with water and, then with nitric acid of $10^{-3}$ mol/L in an amount 30 times as great as the weight of the particulate composite hydrotalcite.

Composition: $Mg_{0.6578}Zn_{0.0088}Al_{0.333}(OH)_2 (CO_3)_{0.167} \cdot 0.5H_2O$
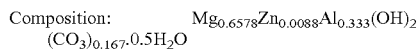

The analytical results of Zn and Na in the particulate composite hydrotalcite and the tested results of the antacid capacity were as shown in Table 1.

EXAMPLE 3

A mixed aqueous solution {solution A} of magnesium nitrate of a concentration of 1.50 mol/L, zinc nitrate of a concentration of $3.08 \times 10^{-3}$ mol/L and aluminum nitrate of a concentration of 0.501 mol/L, an aqueous solution {solution B} of sodium carbonate of a concentration of 0.30 mol/L, and an aqueous solution {solution C} of sodium hydroxide of a concentration of 3.4 N were prepared. Next, the reaction was carried out in the same manner as in Example 1 to obtain a particulate composite hydrotalcite of the following composition. The washing consisted of washing with water and, then with acetic acid of $10^{-3}$ mol/L in an amount 30 times as great as the weight of the particulate composite hydrotalcite.

Composition: $Mg_{0.7485}Zn_{0.0015}Al_{0.25}(OH)_2 (CO_3)_{0.125} \cdot 0.5H_2O$
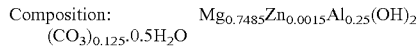

The analytical results of Zn and Na in the particulate composite hydrotalcite and the tested results of the antacid capacity were as shown in Table 1, and the results of the Rossett-Rice test were as shown in Table 2.

EXAMPLE 4

A mixed aqueous solution {solution A} of magnesium nitrate of a concentration of 1.50 mol/L, zinc nitrate of a concentration of $1.733 \times 10^{-2}$ mol/L and aluminum nitrate of a concentration of 0.506 mol/L, an aqueous solution {solution B} of sodium carbonate of a concentration of 0.304 mol/L, and an aqueous solution {solution C} of sodium hydroxide of a concentration of 3.4 N were prepared. Next, the reaction was carried out in the same manner as in Example 1, and the obtained reaction solution was hydrothermally reacted at 150° C. for 12 hours. After cooled, the reaction product was filtered, washed with water, washed with an aqueous solution of sodium carbonate of 0.1 mol/L (0.03 mol) and was washed again with water. Next, the reaction product was washed with hydrochloric acid of $10^{-4}$ mol/L in an amount 40 times as great as the weight of the particulate composite hydrotalcite. The reaction product was dried overnight at 110° C., pulverized and sieved to obtain a particulate composite hydrotalcite of the following composition.

Composition: $Mg_{0.7414}Zn_{0.0086}Al_{0.25}(OH)_2 (CO_3)_{0.125} \cdot 0.5H_2O$
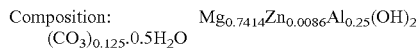

The analytical results of Zn and Na in the particulate composite hydrotalcite and the tested results of the antacid capacity were as shown in Table 1, and the results of the Rossett-Rice test were as shown in Table 2.

EXAMPLE 5

A mixed aqueous solution {solution A} of magnesium sulfate of a concentration of 1.50 mol/L, zinc sulfate of a concentration of $2.9 \times 10^{-3}$ mol/L and aluminum sulfate of a concentration of 0.1879 mol/L, an aqueous solution {solution B} of sodium carbonate of a concentration of 0.23 mol/L, and an aqueous solution {solution C} of sodium hydroxide of a concentration of 3.4 N were prepared. Next, the reaction was carried out in the same manner as in Example 1, and the obtained reaction solution was filtered, washed with water, washed with an aqueous solution of sodium carbonate of a concentration of 0.1 mol/L and was, further washed with water. Next, the reaction solution was washed with hydrochloric acid of $10^{-4}$ mol/L in an amount 40 times as great as the weight of the particulate composite hydrotalcite. The reaction product was dried overnight at 110° C., pulverized and sieved to obtain a particulate composite hydrotalcite of the following composition.

Composition: $Mg_{0.7985}Zn_{0.0015}Al_{0.20}(OH)_2 (CO_3)_{0.0994}(SO_4)_{0.0006} \cdot 0.6H_2O$
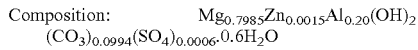

The analytical results of Zn and Na in the particulate composite hydrotalcite and the tested results of the antacid capacity were as shown in Table 1.

EXAMPLE 6

A mixed aqueous solution {solution A} of magnesium sulfate of a concentration of 1.50 mol/L, zinc sulfate of a concentration of $1.627 \times 10^{-2}$ mol/L and aluminum sulfate of a concentration of 0.1895 mol/L, an aqueous solution {solution B} of sodium carbonate of a concentration of 0.23 mol/L, and an aqueous solution {solution C} of sodium hydroxide of a concentration of 3.4 N were prepared. Next, the reaction was carried out in the same manner as in Example 1, and the obtained reaction solution was filtered, washed with water, washed with an aqueous solution of sodium carbonate of a concentration of 0.1 mol/L and was, further washed with water. Next, the reaction solution was washed with acetic acid of $10^{-4}$ mol/L in an amount 40 times as great as the weight of the particulate composite hydrotalcite. The reaction product was dried overnight at 110° C., pulverized and sieved to obtain a particulate composite hydrotalcite of the following composition.

Composition: $Mg_{0.7914}Zn_{0.0086}Al_{0.20}(OH)_2 (CO_3)_{0.0994}(SO_4)_{0.0006} \cdot 0.6H_2O$
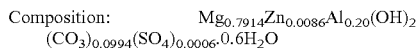

The analytical results of Zn and Na in the particulate composite hydrotalcite and the tested results of the antacid capacity were as shown in Table 1, and the results of the Rossett-Rice test were as shown in Table 2.

EXAMPLE 7

A mixed aqueous solution {solution A} of magnesium chloride of a concentration of 1.50 mol/L, zinc sulfate of a concentration of $2.03 \times 10^{-2}$ mol/L and aluminum chloride of a concentration of 0.507 mol/L, an aqueous solution {solution B} of sodium carbonate of a concentration of 0.30 mol/L, and an aqueous solution {solution C} of sodium hydroxide of a concentration of 3.4 N were prepared. Next, the reaction was carried out in the same manner as in Example 1 to obtain a particulate composite hydrotalcite of the following composition. Washing was conducted by using water and, then nitric acid of $10^{-4}$ mol/L in an amount 40 times as great as the weight of the particulate composite hydrotalcite.

Composition: $Mg_{0.74}Zn_{0.01}Al_{0.25}(OH)_2 (CO_3)_{0.125} \cdot 0.5H_2O$
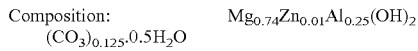

The analytical results of Zn and Na in the particulate composite hydrotalcite and the tested results of the antacid capacity were as shown in Table 1.

EXAMPLE 8

A mixed aqueous solution {solution A} of magnesium chloride of a concentration of 1.20 mol/L, zinc sulfate of a concentration of $1.13 \times 10^{-2}$ mol/L and aluminum chloride of a concentration of 0.404 mol/L, an aqueous solution {solution B} of sodium carbonate of a concentration of 0.24 mol/L, and an aqueous solution {solution C} of sodium hydroxide of a concentration of 3.4 N were prepared. Next, the reaction was carried out in the same manner as in Example 1, and the obtained reaction solution was washed, and the suspension thereof (aqueous system) was hydrothermally reacted at 120° C. for 15 hours. After cooled, the reaction product was filtered, washed, dried overnight at 110° C., pulverized and sieved to obtain a particulate composite hydrotalcite of the following composition. Washing was conducted by using water and, then acetic acid of $10^{-4}$ mol/L in an amount 40 times as great as the weight of the particulate composite hydrotalcite.

Composition: $Mg_{0.743}Zn_{0.007}Al_{0.25}(OH)_2 (CO_3)_{0.125}\cdot 0.5H_2O$

The analytical results of Zn and Na in the particulate composite hydrotalcite and the tested results of the antacid capacity were as shown in Table 1, and the results of the Rossett-Rice test were as shown in Table 2.

EXAMPLE 9

A mixed aqueous solution {solution A} of magnesium chloride of a concentration of 1.20 mol/L, zinc sulfate of a concentration of $4.82 \times 10^{-3}$ mol/L and aluminum chloride of a concentration of 0.402 mol/L, an aqueous solution {solution B} of sodium carbonate of a concentration of 0.24 mol/L, and an aqueous solution {solution C} of sodium hydroxide of a concentration of 3.4 N were prepared. Next, the reaction was carried out in the same manner as in Example 1, and the obtained reaction solution was washed, and the suspension thereof (aqueous system) was hydrothermally reacted at 140° C. for 3 hours. After cooled, the reaction product was filtered, washed, dried overnight at 110° C., pulverized and sieved to obtain a particulate composite hydrotalcite of the following composition. Washing was conducted by using water and, then hydrochloric acid of $10^{-4}$ mol/L in an amount 50 times as great as the weight of the particulate composite hydrotalcite.

Composition: $Mg_{0.747}Zn_{0.003}Al_{0.25}(OH)_2 (CO_3)_{0.125}\cdot 0.5H_2O$

The analytical results of Zn and Na in the particulate composite hydrotalcite and the tested results of the antacid capacity were as shown in Table 1.

EXAMPLE 10

A mixed aqueous solution {solution A} of magnesium chloride of a concentration of 1.20 mol/L, zinc nitrate of a concentration of $7.21 \times 10^{-3}$ mol/L and aluminum chloride of a concentration of 0.604 mol/L, an aqueous solution {solution B} of sodium carbonate of a concentration of 0.36 mol/L, and an aqueous solution {solution C} of sodium hydroxide of a concentration of 3.4 N were prepared. Next, the reaction was carried out in the same manner as in Example 1, and the obtained reaction solution was heated and reacted at 90° C. for 8 hours. After cooled, the reaction product was filtered, washed, dried overnight at 110° C., pulverized and sieved to obtain a particulate composite hydrotalcite of the following composition. Washing was conducted by using water and, then nitric acid of $10^{-5}$ mol/L in an amount 50 times as great as the weight of the particulate composite hydrotalcite.

Composition: $Mg_{0.662}Zn_{0.004}Al_{0.333}(OH)_2 (CO_3)_{0.167}\cdot 0.5H_2O$

The analytical results of Zn and Na in the particulate composite hydrotalcite and the tested results of the antacid capacity were as shown in Table 1.

EXAMPLE 11

A mixed aqueous solution {solution A} of magnesium chloride of a concentration of 1.20 mol/L, zinc nitrate of a concentration of $1.09 \times 10^{-2}$ mol/L and aluminum chloride of a concentration of 0.605 mol/L, an aqueous solution {solution B} of sodium carbonate of a concentration of 0.36 mol/L, and an aqueous solution {solution C} of sodium hydroxide of a concentration of 3.4 N were prepared. Next, the reaction was carried out in the same manner as in Example 1, the obtained reaction solution was washed, and the suspension thereof (aqueous system) was hydrothermally reacted at 130° C. for 4 hours. After cooled, the reaction product was filtered, washed, dried overnight at 110° C. and pulverized to obtain a particulate composite hydrotalcite of the following composition. Washing was conducted by using water and, then acetic acid of $10^{-5}$ mol/L in an amount 50 times as great as the weight of the particulate composite hydrotalcite.

Composition: $Mg_{0.660}Zn_{0.006}Al_{0.333}(OH)_2 (CO_3)_{0.167}\cdot 0.5H_2O$

The analytical results of Zn and Na in the particulate composite hydrotalcite and the tested results of the antacid capacity were as shown in Table 1, and the results of the Rossett-Rice test were as shown in Table 2.

EXAMPLE 12

273 ml of an aqueous solution of sodium hydroxide of 3.4 N and 58 ml of an aqueous solution of sodium carbonate of 1.2 mol/L were introduced into a one-liter container and were stirred at room temperature. In this state, a mixed aqueous solution of 284 ml of an aqueous solution of aluminum chloride of 1.2 mol/L, 10 ml of an aqueous solution of zinc nitrate of 0.7 mol/L and 58 ml of an aqueous solution of aluminum sulfate of 1 mol/L was added thereto. After stirred for one hour, the mixture was transferred into an autoclave, and was hydrothermally reacted at 150° C. for 12 hours. After cooled, the hydrothermally reacted product was filtered, washed with water, washed with 400 ml (0.03 mol) of an aqueous solution of sodium carbonate, washed with water, and was dried overnight at 110° C. Thereafter, the reaction product was pulverized and sieved to obtain a particulate composite hydrotalcite of the following composition.

Composition: $Mg_{0.735}Zn_{0.015}Al_{0.25}(OH)_2 (CO_3)_{0.125}\cdot 0.5H_2O$

The following characteristic peaks were observed in the diffraction pattern of the particulate composite hydrotalcite as measured by the powder X-ray diffraction method.
X-Ray Diffraction Pattern

| Peak No. | 2 θ | d-Value (Å) | Relative intensity ($I/I_0$) |
|---|---|---|---|
| 1 | 11.300 | 7.8240 | 100 |
| 2 | 22.760 | 3.9038 | 50 |

-continued

| Peak No. | 2 θ | d-Value (Å) | Relative intensity (I/I₀) |
|---|---|---|---|
| 3 | 34.340 | 2.6093 | 16 |
| 4 | 38.420 | 2.3411 | 8 |
| 5 | 45.160 | 2.0061 | 6 |
| 6 | 60.360 | 1.5322 | 13 |
| 7 | 61.620 | 1.5039 | 14 |

The analytical results of Zn and Na in the particulate composite hydrotalcite and the tested results of the antacid capacity were as shown in Table 1, and the results of the Rossett-Rice test were as shown in Table 2.

EXAMPLE 13

A mixed aqueous solution {referred to as solution A} of magnesium chloride of a concentration of 0.2 mol/L, zinc nitrate of a concentration of 0.6 mol/L and aluminum sulfate of a concentration of 0.2 mol/L, an aqueous solution {solution B} of sodium carbonate of a concentration of 0.24 mol/L, and an aqueous solution {solution C} of sodium hydroxide of a concentration of 3.4 N were prepared. Next, by using a metering pump, the solution A and the solution B were poured at the same flow rate into a reaction vessel into which de-ionized water has been introduced, and the pH value of the reaction solution was adjusted with the solution C so as to be maintained in a range of 9.0 to 9.5 to form a precipitate. The reaction temperature was 35° C. and the residence time of the reaction solution in the reaction vessel was 30 minutes. The precipitate was filtered, washed, dried overnight at 110° C., pulverized and was sieved to obtain a hydrotalcite compound of the following composition.

Composition: 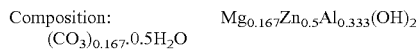 $Mg_{0.167}Zn_{0.5}Al_{0.333}(OH)_2 (CO_3)_{0.167} \cdot 0.5H_2O$ The analytical results of Zn and Na in the particulate composite hydrotalcite and the tested results of the antacid capacity were as shown in Table 1, and the results of the Rossett-Rice test were as shown in Table 2.

COMPARATIVE EXAMPLE 1

A particulate hydrotalcite (trade name: ALCAMAC) manufactured by Kyowa Chemical Industry Co. was used as a gastric antacid. The "ALCAMAC" was a particulate hydrotalcite represented by a chemical formula,

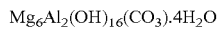 $Mg_6Al_2(OH)_{16}(CO_3) \cdot 4H_2O$

TABLE 1

| Example | Zn (wt %) | Na (ppm) |
|---|---|---|
| 1 | 0.15 | 10 |
| 2 | 0.74 | 8 |
| 3 | 0.13 | 9 |
| 4 | 0.74 | 11 |
| 5 | 0.13 | 10 |
| 6 | 0.74 | 7 |
| 7 | 0.86 | 9 |
| 8 | 0.60 | 6 |
| 9 | 0.25 | 3 |
| 10 | 0.33 | 8 |
| 11 | 0.50 | 5 |
| 12 | 1.15 | 9 |
| 13 | 33 | 9 |
| Comp. Ex. 1 | — | 100 |

TABLE 2

| | Rossett-Rice Test | | | |
|---|---|---|---|---|
| Example | Time till pH becomes 3.0 (min.) | Max. pH | Time in which the pH is adjusted to be 3 to 5 (min.) | Acid-rebound time (min.) (time in which pH is not lower than 5) |
| 1 | 0.10 | 4.36 | 49.9 | 0 |
| 3 | 0.10 | 4.34 | 50.0 | 0 |
| 4 | 0.10 | 4.40 | 49.5 | 0 |
| 6 | 0.10 | 4.38 | 50.1 | 0 |
| 8 | 0.10 | 4.34 | 49.8 | 0 |
| 11 | 0.10 | 4.36 | 50.0 | 0 |
| 12 | 0.10 | 4.36 | 49.9 | 0 |
| 13 | 0.10 | 4.30 | 41.0 | 0 |
| Comp. Ex. 1 | 0.10 | 4.38 | 50.0 | 0 |

EXAMPLE 14

Male rats (SPF) were subjected to an ethanol-induced stomach mucous membrane damage test by using the particulate composite hydrotalcite obtained in Example 12. For the purpose of comparison, the particulate hydrotalcite of Comparative Example 1 (trade name, "ALCAMAC", manufactured by Kyowa Chemical Industry Co.) was also used.
(i) Testing Method.
Test Groups.

| Objects (media) to be tested | 6 rats |
|---|---|
| Particulate composite hydrotalcite, 100 mg/Kg | 6 rats |
| Particulate hydrotalcite (ALCAMAC), 100 mg/Kg | 6 rats |

(ii) Method of Administration.
   Administration passage: oral
   Amount of administration: 5 ml/Kg
   Means of administration: disposable injection cylinder and probe for oral administration
   Period of administration: administered 60 minutes before preparing a stomach mucous membrane damage model
After fasted for about 24 hours, ethanol (99.5%) was orally administered in an amount of 1 ml/rat. After one hour has passed from the administration of ethanol, the blood was removed until dead under anesthesia with pentobarbital sodium (40 mg/Kg, i.p.), and the stomach was removed. 10 ml of a 1% formalin solution was injected into the removed stomach, and the stomach was immersed in the same solution for not shorter than 10 minutes. The stomach was cut open along the greater curvature, and the length of damage that has occurred was measured by using a stereoscopic microscope. The total length per a rat was regarded to be a damage factor. The results were as shown in Table 3. The results prove that the particulate composite hydrotalcite of the present invention works effectively.

EXAMPLE 15

After fasted and kept away from water for about 24 hours, the stomach mucous membrane damage test was conducted by the same method as that of Example 14 but hypodermically administering indometacin in amount of 30 mg/Kg. The results were as shown in Table 4. The results prove that the particulate composite hydrotalcite of the present invention works effectively.

EXAMPLE 16

After fasted for about 24 hours, the stomach mucous membrane damage test was conducted by the same method as that of Example 14 but orally administering aspirin two times each in amount of 125 mg/Kg maintaining an interval of 2 hours. The results were as shown in Table 4. The results prove that the particulate composite hydrotalcite of the present invention works effectively. When the composite hydrotalcite of the present invention was administered, the damage coefficient (mm) greatly decreased as compared to those of Reference Example (no administration) and Comparative Example (ALCAMAC was administered).

TABLE 3

| Drug | Amount of administration (mg/Kg, p.o.) | Number of rats | Damage coefficient (Lesions) (mm) | Inhibition rate (%) |
|---|---|---|---|---|
| Ref. Example[a] | — | 6 | 116.3 ± 20.1 | — |
| Ex. 14 (comp. hydrotalcite) | 100 | 6 | 58.4 ± 13.1 | 50 |
| Comp. Ex. 2 (ALCAMAC) | 100 | 6 | 95.2 ± 14.0 | 18 |

[a] 0.5% MC (MC = methyl cellulose), 5 mL/Kg

TABLE 4

| Drug | Amount of administration (mg/Kg, p.o.) | Number of rats | Damage coefficient (Lesions) (mm) | Inhibition rate (%) |
|---|---|---|---|---|
| Ref. Example[a] | — | 6 | 13.4 ± 3.2 | — |
| Ex. 15 (comp. hydrotalcite) | 100 | 6 | 8.5 ± 3.4 | 37 |
| Comp. Ex. 2 (ALCAMAC) | 100 | 6 | 12.4 ± 3.1 | 7 |

[a] 0.5% MC, 5 mL/Kg

The invention claimed is:

1. A method of suppressing damage to a stomach inner wall by reducing the number of ulcers in an internal wall of a stomach in a mammal, comprising orally administering to said mammal in need thereof an effective amount of a particulate composite hydrotalcite presented by the following formula (1), $$(Mg_aZn_b)_{1-x}Al_x(OH)_2(A^{n-})_{x/n} \cdot mH_2O \quad (1)$$

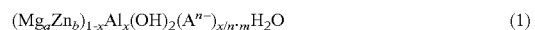

wherein $A^{n-}$ is $CO_3^{2-}$, $SO_4^{2-}$ or $Cl^-$, n is 1 or 2, and x, a, b and m are values that satisfy the following conditions, $0.18 \leq x \leq 0.4$, $0.5 \leq a < 1$, $0 < b \leq 0.5$, $0 \leq m < 1$.

2. The method according to claim 1, wherein An- of the hydrotalcite is $CO_3^{2-}$ or $SO_4^{2-}$.

3. The method according to claim 1, wherein x of the hydrotalcite satisfies $0.2 \leq x \leq 0.35$.

4. The method according to claim 1, wherein b of the hydrotalcite satisfies $0.0005 \leq b \leq 0.2$.

5. The method according to claim 1, wherein a of the hydrotalcite satisfies $0.6 \leq a \leq 0.9$.

6. A method of treating gastric acid and suppressing damage to a mucous membrane of an internal wall of a stomach by reducing the number of ulcers comprising:

orally administering to a mammal in need thereof an effective amount of a particulate composite hydrotalcite presented by the following formula (1), $$(Mg_aZn_b)_{1-x}Al_x(OH)_2(A^{n-})_{x/n} \cdot mH_2O \quad (1)$$

wherein $A^{n-}$ is $CO_3^{2-}$, $SO_4^{2-}$ or $Cl^-$, n is 1 or 2, and x, a, b and m are values that satisfy the following conditions, $0.18 \leq x \leq 0.4$, $0.5 \leq a < 1$, $0 < b \leq 0.5$, $0 \leq m < 1$, thereby treating gastric acid, suppressing damage to the mucous membrane of the internal wall of the stomach, and inhibiting the occurrence of ulcers.

* * * * *